(12) United States Patent
Fogwill et al.

(10) Patent No.: US 10,371,673 B2
(45) Date of Patent: Aug. 6, 2019

(54) CARBON DIOXIDE BASED CHROMATOGRAPHY SYSTEMS INCLUDING MULTIPLE CARBON DIOXIDE PUMPS

(71) Applicant: Waters Technologies Corporation, Milford, MA (US)

(72) Inventors: Michael O. Fogwill, South Grafton, MA (US); Joseph A. Jarrell, Newton Highlands, MA (US); Joseph D. Michienzi, Plainville, MA (US); Thomas S. McDonald, Littleton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 15/909,264

(22) Filed: Mar. 1, 2018

(65) Prior Publication Data

US 2018/0252684 A1    Sep. 6, 2018

Related U.S. Application Data

(60) Provisional application No. 62/466,537, filed on Mar. 3, 2017.

(51) Int. Cl.
*G01N 30/32* (2006.01)
*G01N 30/34* (2006.01)
(Continued)

(52) U.S. Cl.
CPC ........... *G01N 30/32* (2013.01); *B01D 15/163* (2013.01); *B01D 15/40* (2013.01); *G01N 30/34* (2013.01);
(Continued)

(58) Field of Classification Search
CPC .... G01N 30/32; G01N 30/36; G01N 30/7233; G01N 2030/326; B01D 15/163; B01D 15/40
See application file for complete search history.

(56) References Cited

U.S. PATENT DOCUMENTS 4,628,743 A * 12/1986 Miller, Jr. ............. G01F 1/7044
                                                    73/204.25
4,871,453 A * 10/1989 Kumar ................... G01N 30/28
                                                     210/198.2

(Continued)

FOREIGN PATENT DOCUMENTS

JP    H06289001 A    10/1994
JP    2015194363 A   11/2015

OTHER PUBLICATIONS

Chester,T.L., et al., "Pressure-Regulating Fluid Interface and Phase Behavior Considerations in the Voupling of Packed-Column Supercritical Fluid Chromatography with Low Pressure Detectors," Journal of Chromatography A. 807:2 265-273 (1998).

(Continued)

*Primary Examiner* — Justin N Olamit
(74) *Attorney, Agent, or Firm* — Womble Bond Dickinson; Deborah M. Vernon; Heath T. Misley (57) ABSTRACT

The present disclosure relates to methodologies, systems and apparatus for controlling pressure in a $CO_2$-based chromatography system. A first $CO_2$ pump operates in constant flow mode and delivers $CO_2$ to a chromatography column, and liquid modifier is introduced to the chromatography column according to a gradient. A second $CO_2$ pump is disposed downstream of the column and operates in constant pressure mode to introduce $CO_2$ into a flow stream at an output of the column. Liquid modifier is also introduced into the flow stream at the output of the column according to a (Continued)

reverse gradient compared to the gradient entering the chromatography column.

10 Claims, 10 Drawing Sheets

(51) Int. Cl.
- *G01N 30/72* (2006.01)
- *G01N 30/36* (2006.01)
- *B01D 15/16* (2006.01)
- *B01D 15/40* (2006.01)
- *G01N 30/62* (2006.01)

(52) U.S. Cl.
CPC ............. *G01N 30/36* (2013.01); *G01N 30/62* (2013.01); *G01N 30/7233* (2013.01); *G01N 2030/326* (2013.01); *G01N 2030/347* (2013.01); *G01N 2030/623* (2013.01)

(56) References Cited

U.S. PATENT DOCUMENTS

| | | | |
|---|---|---|---|
| 6,358,414 B1* | 3/2002 | Maiefski | B01D 15/08 137/334 |
| 8,877,051 B2* | 11/2014 | Fogelman | G01N 30/82 210/143 |
| 9,694,301 B2* | 7/2017 | Choikhet | G01N 30/463 |
| 2013/0180404 A1 | 7/2013 | Fogelman et al. | |
| 2015/0101393 A1* | 4/2015 | Fogwill | G01F 1/76 73/23.31 |
| 2015/0301000 A1* | 10/2015 | Fogwill | G01N 30/68 436/160 |

OTHER PUBLICATIONS

International Search Report and Written Opinion from corresponding application PCT/IB2018/051324, completed on Jun. 14, 2018 and dated May 31, 2018.

* cited by examiner (Prior Art)
FIG. 1

CARBON DIOXIDE BASED CHROMATOGRAPHY SYSTEMS INCLUDING MULTIPLE CARBON DIOXIDE PUMPS

RELATED APPLICATIONS

This application claims the benefit of U.S. Provisional Patent Application 62/466,537 filed on Mar. 3, 2017 titled "CARBON DIOXIDE BASED CHROMATOGRAPHY SYSTEMS INCLUDING MULTIPLE CARBON DIOXIDE PUMPS," the contents of which are incorporated herein by reference in its entirety.

TECHNICAL FIELD

The present disclosure relates to techniques for controlling pressure in carbon dioxide chromatography systems. The present disclosure also relates to methodologies, systems and apparatus for controlling pressure downstream of a chromatography column.

BACKGROUND OF THE TECHNOLOGY

Chromatography involves the flowing of a mobile phase over a stationary phase to effect the separation of analytes of interest. To speed-up and enhance the efficiency of the separation, pressurized mobile phases were introduced. Carbon dioxide based chromatographic systems use $CO_2$ as a component of the mobile phase, and the $CO_2$ based mobile phase is delivered from a pump and carried through the separation column as a pressurized fluid. In systems using $CO_2$ as a mobile phase component, one challenge is transferring the analyte and ensuring $CO_2$ and co-solvent miscibility downstream of the column. The changes in co-solvent and analyte solubility in the $CO_2$-based mobile phase become especially problematic due to the extreme changes in density experienced when interfacing the $CO_2$-based mobile phase to low pressure detection, such as flame ionization detection or mass spectrometry. Therefore, a need exists for chromatography systems that provide increased stability and control of temperature and pressure levels.

BRIEF SUMMARY OF THE TECHNOLOGY

Exemplary embodiments of the present technology are directed to systems for controlling pressure and mobile phase flow rates in chromatography systems. In particular, some embodiments are related to methodologies, systems and apparatus that are used in $CO_2$-based chromatography systems, i.e., a chromatography system in which the mobile phase includes $CO_2$. Further, the embodiments are related to methodologies, systems and apparatus that employ one, two, or potentially more $CO_2$ pumps.

In one aspect, the present technology relates to a $CO_2$-based chromatography system including a first $CO_2$ pump disposed to deliver $CO_2$ to a chromatography column. The system also includes a first liquid modifier pump disposed to deliver a liquid modifier to the chromatography column. The system also includes a second $CO_2$ pump located downstream of the column and disposed to operate independently of the first $CO_2$ pump to introduce $CO_2$ into a flow stream at an output of the column. The second $CO_2$ pump operates in constant pressure mode in order to maintain a target pressure. The system also includes a second liquid modifier pump located downstream of the column and disposed to operate independently of the first liquid modifier pump to introduce liquid modifier into the flow stream at the output of the column. The second liquid modifier pump is also disposed to deliver liquid modifier according to a reverse gradient compared to a gradient entering the column via the first liquid modifier pump.

Embodiments of this aspect of the technology can include one or more of the following features. In some embodiments, the system includes a detector located downstream of the second $CO_2$ pump and the second liquid modifier pump. In some embodiments, the detector is a flame ionization detector or a mass spectrometer. In some embodiments, the second liquid modifier pump maintains a total flow rate of liquid modifier entering the detector constant. In some embodiments, the first $CO_2$ pump is disposed to operate in a constant flow mode, and the second $CO_2$ pump is disposed to operate in a constant pressure mode. In some embodiments, the second $CO_2$ pump maintains system pressure downstream of the column at a target value. In some embodiments, the second $CO_2$ pump and the second liquid modifier pump introduce fluid at the output of the column via a tee fitting or a cross fitting. In some embodiments, the second $CO_2$ pump and the second liquid modifier pump introduce fluid at the output of the column via a cross fitting. In some embodiments, the system also includes a restrictor. In some embodiments, the restrictor is disposed to connect the output of the tee fitting to a detector.

In another aspect, the present technology relates to a method of maintaining pressure in a $CO_2$-based chromatography system. The method includes introducing $CO_2$ into a mixer via a first $CO_2$ pump. The method also includes introducing liquid modifier into the mixer via a first liquid modifier pump. The method also includes receiving a mixture of $CO_2$ and liquid modifier from the mixer at a chromatography column. The method also includes introducing $CO_2$ into a flow stream at an output of the column via a second $CO_2$ pump. The method also includes introducing liquid modifier into the flow stream at the output of the column via a second liquid modifier pump. The method also includes controlling the second $CO_2$ pump to operate in constant pressure mode to maintain a target pressure downstream of the column, and controlling the second liquid modifier pump to deliver liquid modifier according to a reverse gradient compared to a gradient introduced into the column from the first liquid modifier pump.

Embodiments of this aspect of the technology can include one or more of the following features. In some embodiments, the method also includes introducing the flow stream at the output of the column into a detector. In some embodiments, the method also includes controlling the second liquid modifier pump such that a total flow rate of liquid modifier entering the detector is constant. In some embodiments, the detector is a flame ionization detector or a mass spectrometer. In some embodiments, the first $CO_2$ pump operates in a constant flow mode, and the second $CO_2$ pump operates in a constant pressure mode. In some embodiments, the second $CO_2$ pump maintains system pressure downstream of the column at a target value. In some embodiments, the second $CO_2$ pump and the second liquid modifier pump introduce fluid at the output of the column via a tee fitting. In some embodiments, the method also includes directing an output of the tee fitting to a detector via a fixed restrictor.

In another aspect, the present technology relates to a $CO_2$-based chromatography system including a first $CO_2$ pump disposed to deliver $CO_2$ to a chromatography column. The system also includes a liquid modifier pump. The system also includes a second $CO_2$ pump located downstream of the column and disposed to operate independently of the first $CO_2$ pump to introduce $CO_2$ into a flow stream at an output of the column. The second $CO_2$ pump operates in constant pressure mode in order to maintain a target pressure. The system also includes an active splitter disposed to receive a liquid modifier from the liquid modifier pump and deliver liquid modifier to the chromatography column according to a gradient. The active splitter is also disposed to introduce liquid modifier at the output of the column according to a reverse gradient compared to the gradient entering the chromatography column.

In another aspect, the present technology relates to a $CO_2$-based chromatography system including a $CO_2$ pump, a liquid modifier pump, a first active splitter, and a second active splitter. The first active splitter is disposed to receive a liquid modifier from the liquid modifier pump, introduce the liquid modifier to a chromatography column according to a gradient, and introduce the liquid modifier into a flow stream downstream of the chromatography column according to a reverse gradient compared to the gradient entering the chromatography column. The second active splitter is disposed to receive $CO_2$ from the $CO_2$ pump, introduce $CO_2$ to the chromatography column, and introduce $CO_2$ into the flow stream downstream of the chromatography column to maintain a target pressure.

The above aspects of the technology provide one or more of the following advantages. Some embodiments of the technology allow for the decoupling of mobile phase flow rate and system pressure at flow rates below which a BPR is ineffective. Some embodiments of the technology also allow for changes to be made to the mobile phase composition without requiring re-optimization of a detector, such as, for example a mass spectrometer.

BRIEF DESCRIPTION OF THE DRAWINGS

The foregoing and other features and advantages provided by the present disclosure will be more fully understood from the following description of exemplary embodiments when read together with the accompanying drawings presented below.

DETAILED DESCRIPTION OF THE TECHNOLOGY

Provided herein are methodologies, systems, and apparatus for maintaining pressure in a $CO_2$-based chromatography system using two $CO_2$ pumps. Interfacing $CO_2$-based chromatography systems to low pressure detection (e.g., flame ionization detection or mass spectrometry) poses a unique challenge due to the intricacies of managing analyte and co-solvent solubility in carbon dioxide as the mobile phase transitions from a pressurized state to a gas or ambient pressure state. In $CO_2$-based chromatography systems, a fixed restrictor can be used to divert a portion of the mobile phase flow to detection. However, such a restrictor may be unable to adapt to changes in system pressure or fluid composition. As a result of this inability to adapt, any change in system pressure or fluid composition will affect the portion of the mobile phase directed to detection.

In prior art systems, in which pressure control had been implemented, undesirable effects have previously been experienced due analyte precipitation (analyte loss), which prevents accurate and repeatable detection. A BPR can be employed in $CO_2$-based chromatography systems to control system pressure over a wide range of mobile phase flow rates (i.e. decouple the flow rate and pressure). At the analytical scale, employing a BPR can decouple the mobile phase flow rate from the system pressure. The BPR can maintain a set system pressure while a pump operating in constant-flow mode can establish the flow rate of the mobile phase through the column. However, challenges arise when interfacing analytical-scale $CO_2$-based chromatography systems to low-pressure detection (i.e. flame ionization detection or mass spectrometry) due to the intricacies of managing analyte solubility as the mobile phase transitions from a pressurized state to a low-pressure gaseous state. BPRs can be ineffective at regulating system pressures at small-scale mobile phase flow rates (i.e. microfluidic, capillary, or packed capillary). Since the density of the mobile phase is proportional to solvating power, mobile phase decompression can result in analyte precipitation. Also, when operating with a liquid co-solvent or liquid modifier, the depressurized carbon dioxide no longer has the ability to dissolve the modifier. Therefore, the mobile phase stream downstream of the BPR consists of pockets of gaseous $CO_2$ pushing pockets of liquid modifier. This heterogeneous flow results in a very inconsistent detector signal. Considering these factors, it is therefore unwise to interface to a low-pressure detector after the BPR (i.e. after the mobile phase has decompressed). Further, most BPRs contain considerable dead volume, which can cause a significant loss in chromatographic performance when an analyte of interest traverses the BPR. In order to address this interface issue, it is common to employ a split-flow interface when employing a BPR. Split flow interfaces can result in reduction of sensitivity and uncertainty in quantitation. In order to address these issues encountered with BPRs, a method of employing two autonomous $CO_2$ pumps is herein disclosed in order to independently control system pressure and flow rate at any scale within a $CO_2$-based chromatography system.

Figure 1:
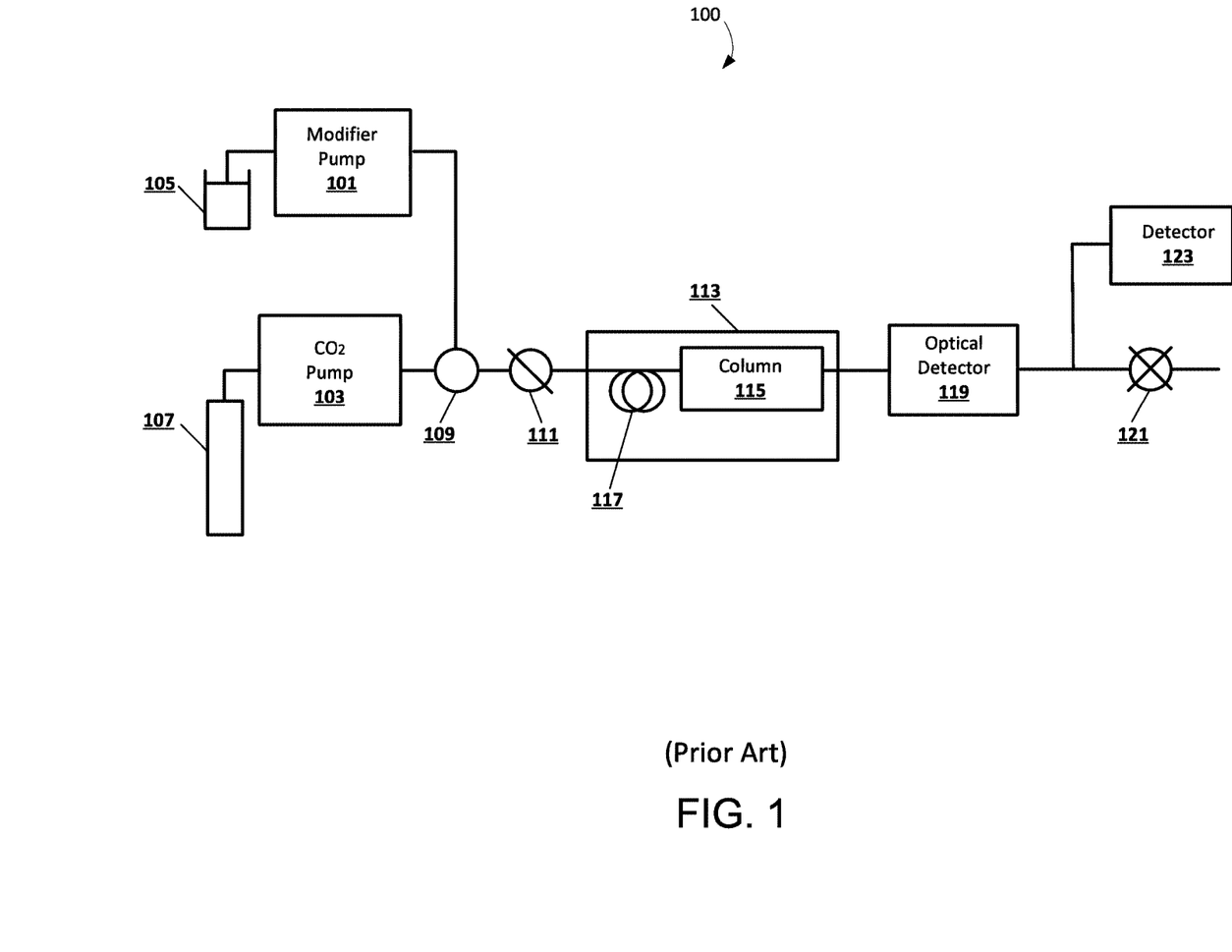
FIG. 1 is a block diagram illustrating an exemplary prior art chromatography system with a single $CO_2$ pump and a back pressure regulator.

FIG. 1 is a block diagram illustrating an exemplary prior art chromatography system 100 with a single $CO_2$ pump and a BPR. In this example, a modifier pump 101 is used to pump a liquid modifier from a solvent reservoir 105 to a mixer 109, and a $CO_2$ pump 103 is used to pump $CO_2$ from a $CO_2$ container 107 to the mixer 109. In this technological field, $CO_2$ pumps are pumps that are able to adequately pump $CO_2$ and often require cooling to maintain the $CO_2$ in a liquid-like state. The liquid modifier and $CO_2$ mixture can be injected to a chromatography column 115 via an injector 111. In this example, the $CO_2$-based chromatography column 115 is located within a column oven 113, which includes preheating elements 117. An optional optical detector 119 may be located at the output of the chromatography column 115, in some embodiments. A portion of the analyte is diverted to a detector 123, and a BPR 121 is located downstream of the column 115 to control pressure downstream of the column. In some examples, the detector 123 is a flame ionization detector.

In the example shown in FIG. 1, the analyte peak does not traverse the BPR 121 en-route to low-pressure detection and retains its chromatographic fidelity. Further, with proper restrictor design, the mobile phase retains appreciable solvating power until the analyte is near the point of detection within the detector. As will be appreciated, the point of detection or point of ionization may be within a flame or a spray plume. Only at this point is the mobile phase allowed to decompress. In this way, the split-flow interface addresses the challenges encountered when interfacing a system with a BPR to a low-pressure detector. However, split-flow interface chromatography systems often utilize a fixed restrictor, and any change to the mobile phase flow rate, system pressure, or mobile phase viscosity will result in a change in the split ratio, and therefore interfere with quantitation. Additionally, since only a fraction of the analyte is diverted to the detector 123, sensitivity is proportionally lower when employing a split-flow interface to detection. The BPR 121 may be unable to control system pressure at very low mobile phase flow rates, such as those encountered in microfluidic, capillary, or packed capillary scale separations. Historically, in small-scale $CO_2$-based chromatography separations, fixed restrictors (i.e. not variable) have been employed in place of BPRs to control system pressure. This approach is also applicable to analytical-scale separations and allows for the full-flow introduction of the mobile phase to detection.

Figure 2:
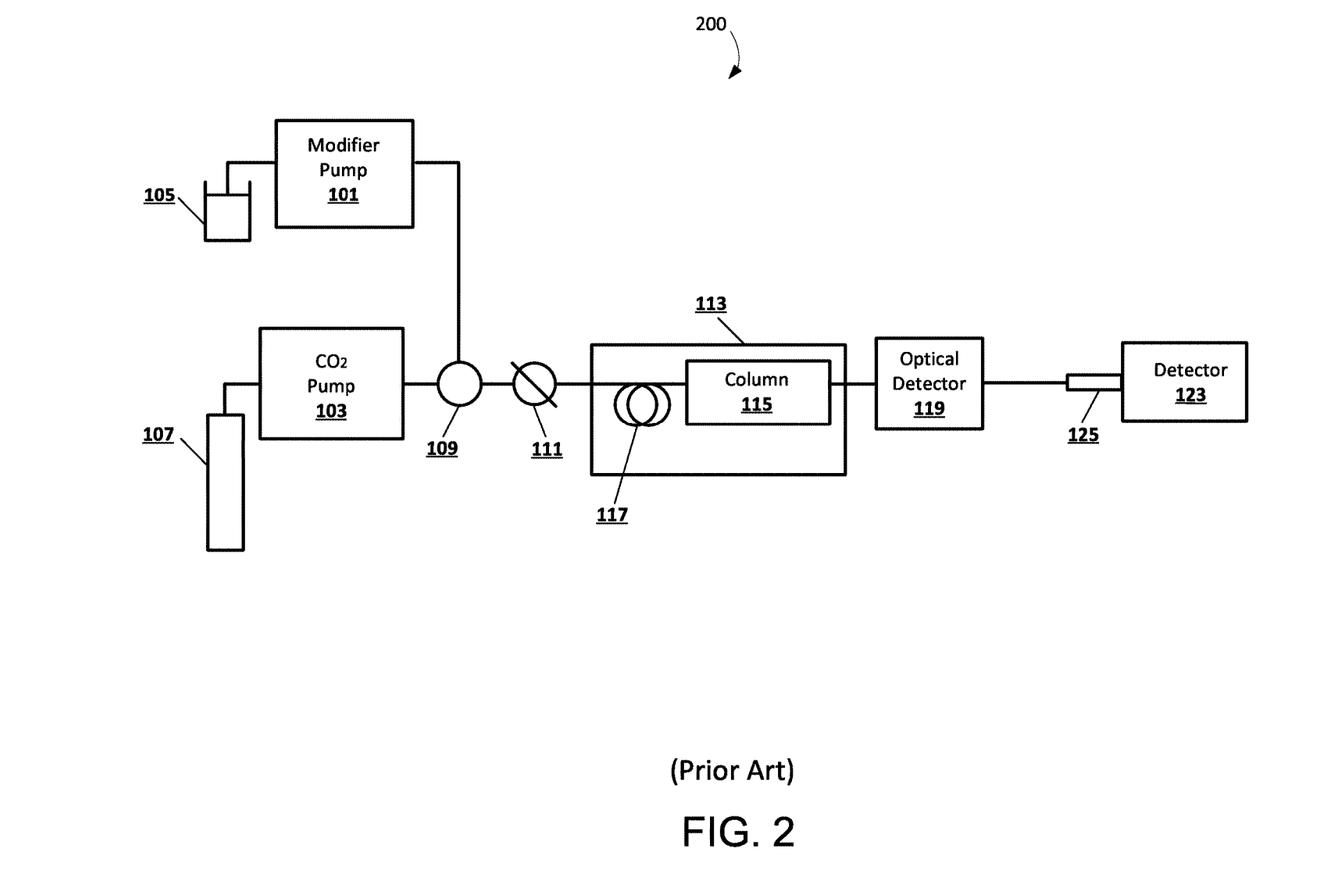
FIG. 2 is a block diagram illustrating an exemplary prior art chromatography system with a single $CO_2$ pump and a fixed restrictor.

FIG. 2 is a block diagram illustrating an exemplary prior art chromatography system 200 with a single $CO_2$ pump and a fixed restrictor. In this example, a modifier pump 101 is used to pump a liquid modifier from a solvent reservoir 105 to a mixer 109, and a $CO_2$ pump 103 is used to pump $CO_2$ from a $CO_2$ container 107 to the mixer 109. The liquid modifier and $CO_2$ mixture can be injected to a chromatography column 115 via a sample injector 111. In this example, the $CO_2$-based chromatography column 115 is located within a column oven 113, which includes preheating elements 117. An optional optical detector 119 may be located at the output of the chromatography column 115. A fixed restrictor 125 is located downstream of the column 115 and upstream of a detector 123. In some examples, the detector 123 is a flame ionization detector. In some examples, the detector 123 is a mass spectrometer. In the example shown in FIG. 2, the $CO_2$ pump 103 operates in constant flow mode, and the restrictor 125 controls the post-column pressure of the mobile phase. One obstacle encountered when employing a fixed restrictor arises when it is desirable to change the flow rate of the mobile phase or the system pressure. A fixed restrictor can cause an increase in system pressure when increasing the flow rate of the mobile phase (i.e. increasing the chromatographic pump flow rate). Therefore, the flow rate and system pressure are not decoupled, and require a hardware change (i.e. replace the restrictor) when an independent change in either flow rate or system pressure is desired. Another obstacle encountered when employing a fixed restrictor arises when a property of the mobile phase, such as viscosity or composition, is altered. Such changes in mobile phase properties are commonly encountered when employing composition-programmed gradient separations. A change in the composition of the mobile phase results in a change in the viscosity of the fluid and/or a change in the flow rate of the decompressing fluid. As such, since the fixed restrictor 125 is unable to adapt to these changing properties of the mobile phase, the fixed restrictor 125 is unable to maintain the post-column pressure at a constant value.

Figure 3:
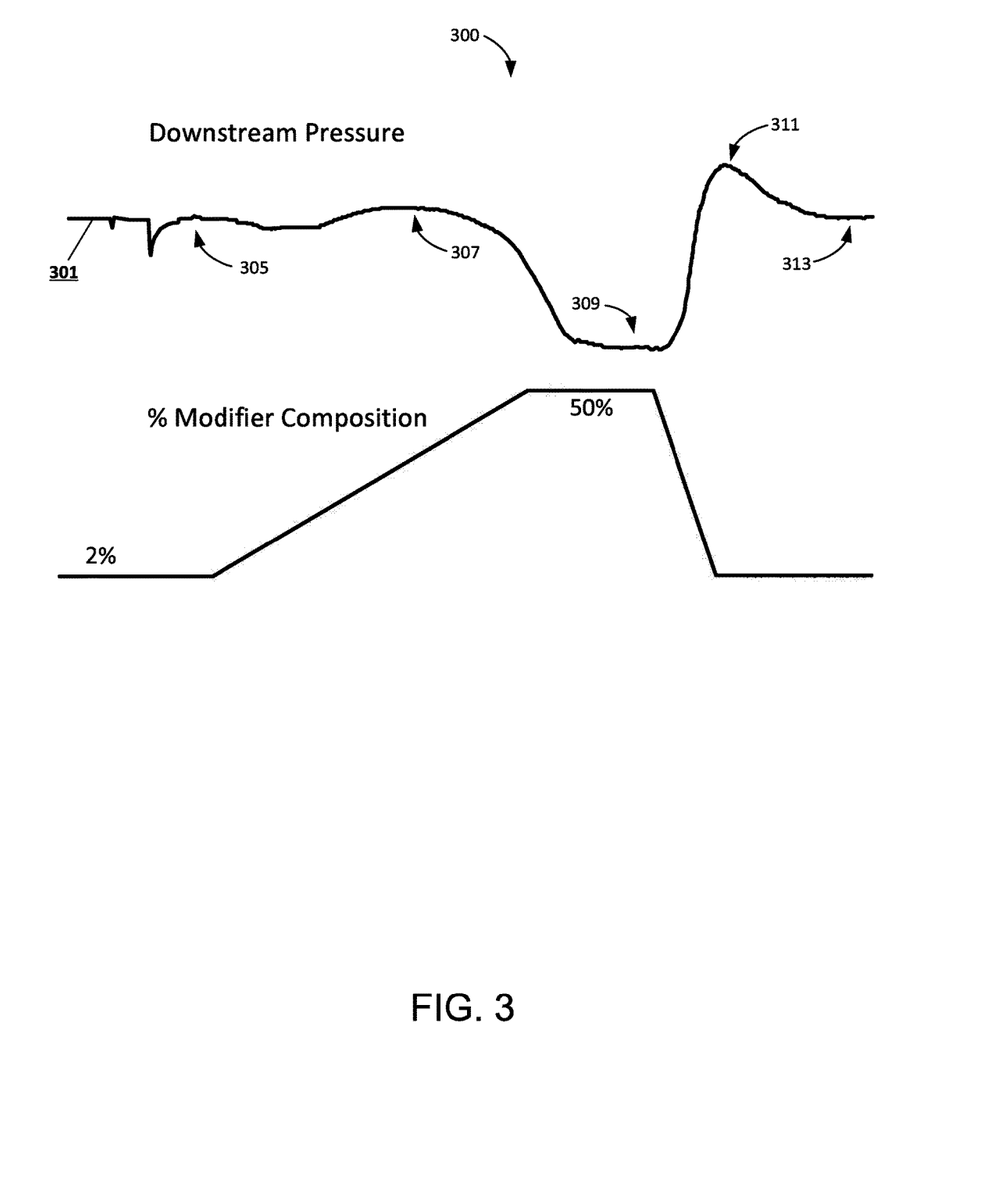
FIG. 3 is a graph representing the relationship between mobile phase composition and back pressure generated by a fixed restrictor.

FIG. 3 is a graph 300 representing the relationship between mobile phase composition and back pressure generated by a fixed restrictor. In this example, the graph 301 illustrates the downstream pressure generated by the fixed restrictor. In this example, the downstream pressure begins at about 1,810 PSI at region 305 when the modifier composition is around 2% and slowly increases to about 1,860 PSI in region 307 as the composition of the mobile phase approaches 30%. When the modifier composition reaches about 50%, the downstream pressure drops to about 1,230 PSI in region 309, and spikes to about 2,030 PSI in region 311 after the modifier percentage drops again. Once the modifier percentage has dropped to about 2% again, the downstream pressure returns to about 1,810 PSI at region 313. As seen in this figure, the post-column pressure varies considerably as the composition gradient progresses. The uncontrolled post-column pressure in this instance can cause undesirable mobile phase properties resulting from operation in a compressible region of the phase diagram (e.g., an area where slight temperature and/or pressure changes have drastic effects on density), or resulting in the loss of miscibility between the modifier and $CO_2$.

Figure 4A:
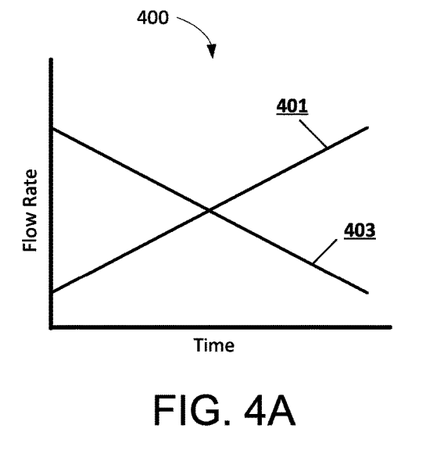
FIG. 4A is a graph of the flow rate for the upstream co-solvent and upstream $CO_2$ for a $CO_2$-based chromatography system where a downstream co-solvent is introduced using a downstream pump in constant pressure mode.
Figure 4B:
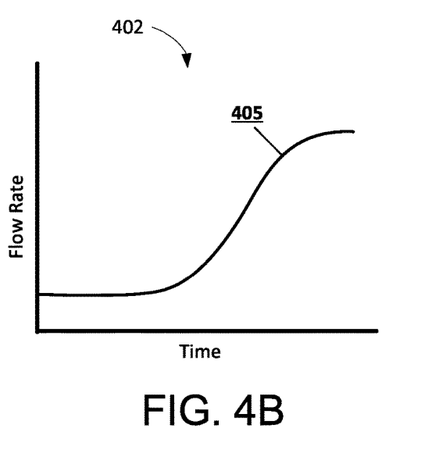
FIG. 4B is a graph of the flow rate for the downstream co-solvent for a $CO_2$-based chromatography system where a downstream co-solvent is introduced using a downstream pump in constant pressure mode.
Figure 4C:
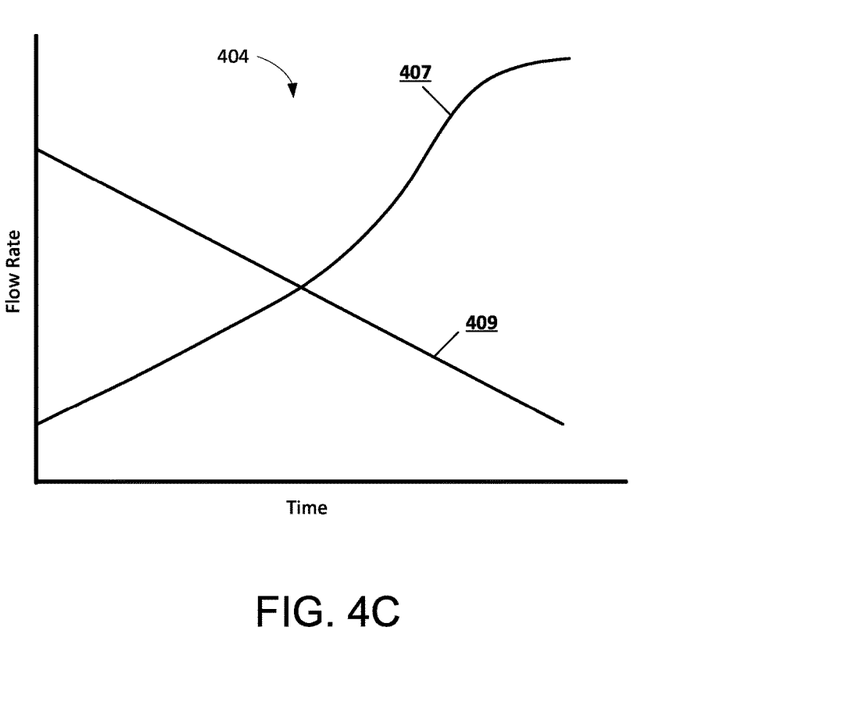
FIG. 4C is a graph of the net co-solvent flow rate and the net $CO_2$ flow rate for a $CO_2$-based chromatography system where a downstream co-solvent is introduced using a downstream pump in constant pressure mode.

FIGS. 4A-4C show graphs of flow rates for a $CO_2$-based chromatography system where a downstream co-solvent, or liquid modifier, is introduced using a downstream pump in constant pressure mode. The downstream co-solvent can also be referred to as a makeup fluid, which may be the same composition as the upstream co-solvent or a different composition. FIG. 4A shows a graph 400 of the flow rate for the upstream co-solvent and upstream $CO_2$. FIG. 4B shows a graph 402 of the flow rate for the downstream co-solvent using a downstream pump in constant pressure mode. FIG. 4C shows a graph 404 of the net co-solvent flow rate and the net $CO_2$ flow rate using a downstream pump in constant pressure mode. As the gradient progresses, graph 401 shows an increase in upstream co-solvent flow rate and graph 403 shows a decrease in upstream $CO_2$ flow rate. Graph 405 shows how the downstream co-solvent flow rate increases as the gradient progresses. The net $CO_2$ flow rate, shown in graph 409 decreases as the gradient progresses, and the net co-solvent flow rate increases as the gradient progresses. This increase in net co-solvent flow rate can lead to detector disruption of the optimal detector response. Another obstacle encountered when employing a fixed restrictor arises when a property of the mobile phase, such as viscosity or composition, is altered. Such changes in mobile phase properties are commonly encountered when employing composition-programmed gradient separations.

Systems and methods of the present technology are advantageous because they allow for the decoupling of mobile phase flow rate and system pressure at flow rates below which a BPR is ineffective (i.e. microfluidic implementation). The techniques described herein also address the problems of band spread and analyte loss when employing post-BPR detection with a $CO_2$-based chromatography system. In general, the systems and methods feature two $CO_2$ pumps, where a first $CO_2$ pump is positioned upstream of the column to introduce $CO_2$ into the column in a constant flow mode, and a second $CO_2$ pump is positioned downstream of the column to introduce $CO_2$ into a flow stream at the output of the column in constant pressure mode. This method of decoupling flow and pressure could be easily adapted to $CO_2$-based chromatography systems operating with preparative, semi-preparative, analytical, or capillary-scale packed-bed columns or open tubular columns. The columns could be prepared in metallic, fused silica, or polymeric tubes or in metallic, ceramic, glass, or various polymeric microfluidic platforms. Further, this technology could potentially be utilized in high pressure gas chromatography (GC), or solvating GC separations.

Figure 5:
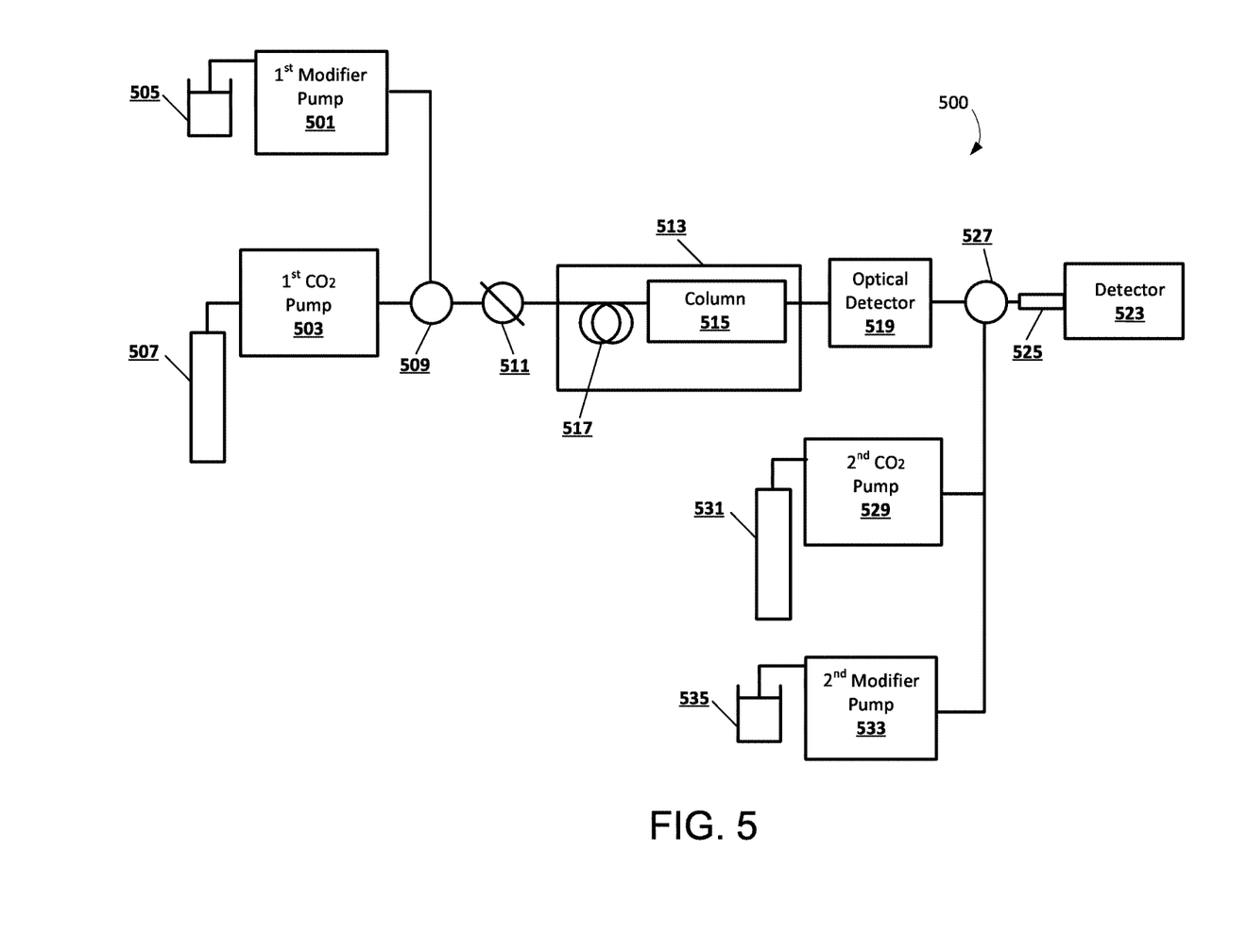
FIG. 5 is a block diagram illustrating an exemplary $CO_2$-based chromatography system with two $CO_2$ pumps, according to embodiments of the present disclosure.

FIG. 5 is a block diagram illustrating an exemplary $CO_2$-based chromatography system 500 with two $CO_2$ pumps, according to embodiments of the present disclosure. In exemplary embodiments, a second $CO_2$ pump is added to the system in place of a BPR, downstream of the chromatography column, in order to control system pressure. In this example, a first modifier pump 501 is used to pump a liquid modifier from a solvent reservoir 505 to a mixer 509, and a first $CO_2$ pump 503 is used to pump $CO_2$ from a $CO_2$ container 507 to the mixer 509. The liquid modifier and $CO_2$ mixture can be injected to a chromatography column 515 via a sample injector 511. The first $CO_2$ pump 503 and the first modifier pump 501 are disposed to transmit a mixture of $CO_2$ and liquid modifier to the chromatography column 515 according to a gradient. In this example embodiment, the $CO_2$-based chromatography column 515 is located within a column oven 513, which includes preheating elements 517. An optional optical detector 519 may be located at the output of the chromatography column 515. The first $CO_2$ pump 503 is operated in constant flow mode and is responsible for maintaining a constant flow rate of the mobile phase across the column 515. A second $CO_2$ pump 529 is located downstream of the column 515 and can be connected to the system using, for example, a tee fitting 527 or a cross fitting. Similarly, a second modifier pump 533 can be connected to the system also downstream of the column 515. In exemplary embodiments, the second modifier pump can introduce the same liquid as the first modifier pump 501. The second $CO_2$ pump 529 is operated in constant pressure mode and is responsible for maintaining the system pressure. Since the first $CO_2$ pump 503 and the second $CO_2$ pump 529 are operated independently, the system flow rate and system pressure are effectively decoupled. A fixed restrictor 525 is located downstream of the second $CO_2$ pump 529 and upstream of a detector 523. The fixed restrictor 525 may be a linear, tapered, converging-diverging, integral, or fritted restrictor. In some examples, the detector 523 is a flame ionization detector. In some examples, the detector 523 is a mass spectrometer. The second $CO_2$ pump 529 can pump $CO_2$ from a second $CO_2$ container 531, while the second modifier pump 533 can pump a liquid modifier from a second solvent reservoir 535. As will be appreciated, the first $CO_2$ container 507 and the second $CO_2$ container 531 could be a single container. That is containers 507 and 531 could be from a single primary source and delivered to the respective pumps. Likewise, the first solvent reservoir 505 and the second solvent reservoir 535 could be provided from a single reservoir, in some embodiments.

In exemplary embodiments, in order to reduce the magnitude of change of the mobile phase composition across the gradient while employing a pressure-controlled pump, a pressure controlling fluid gradient can be employed. In this particular example, the second $CO_2$ pump 529 and second modifier pump 533 transmit a pressure controlling fluid mixture to the flow stream at the output of the chromatography column 515. This pressure controlling fluid includes a mixture of $CO_2$ and liquid modifier, and is introduced at the output of the chromatography column according to a reverse gradient of the first $CO_2$ pump 503 and first modifier pump 501. In some examples, the second modifier flow gradient may be time aligned relative to the first modifier pump gradient in order to compensate for system volume. In this manner, the total flow rate of liquid entering the detector 523 is constant over the entire composition-programmed gradient separation. Because a single liquid modifier fluid cannot compensate for the reduced pressure experienced when the $CO_2$ flow rate is reduced as the gradient progresses, the pressure controlling fluid is a binary mixture of $CO_2$ and liquid modifier, and the second $CO_2$ pump 529 is operated in a constant pressure mode. In this regard, the total amount of liquid entering the detector 523 is fixed, the tuning parameters are more closely matched to all regions of the gradient, and the system pressure can be accurately controlled.

Figure 6:
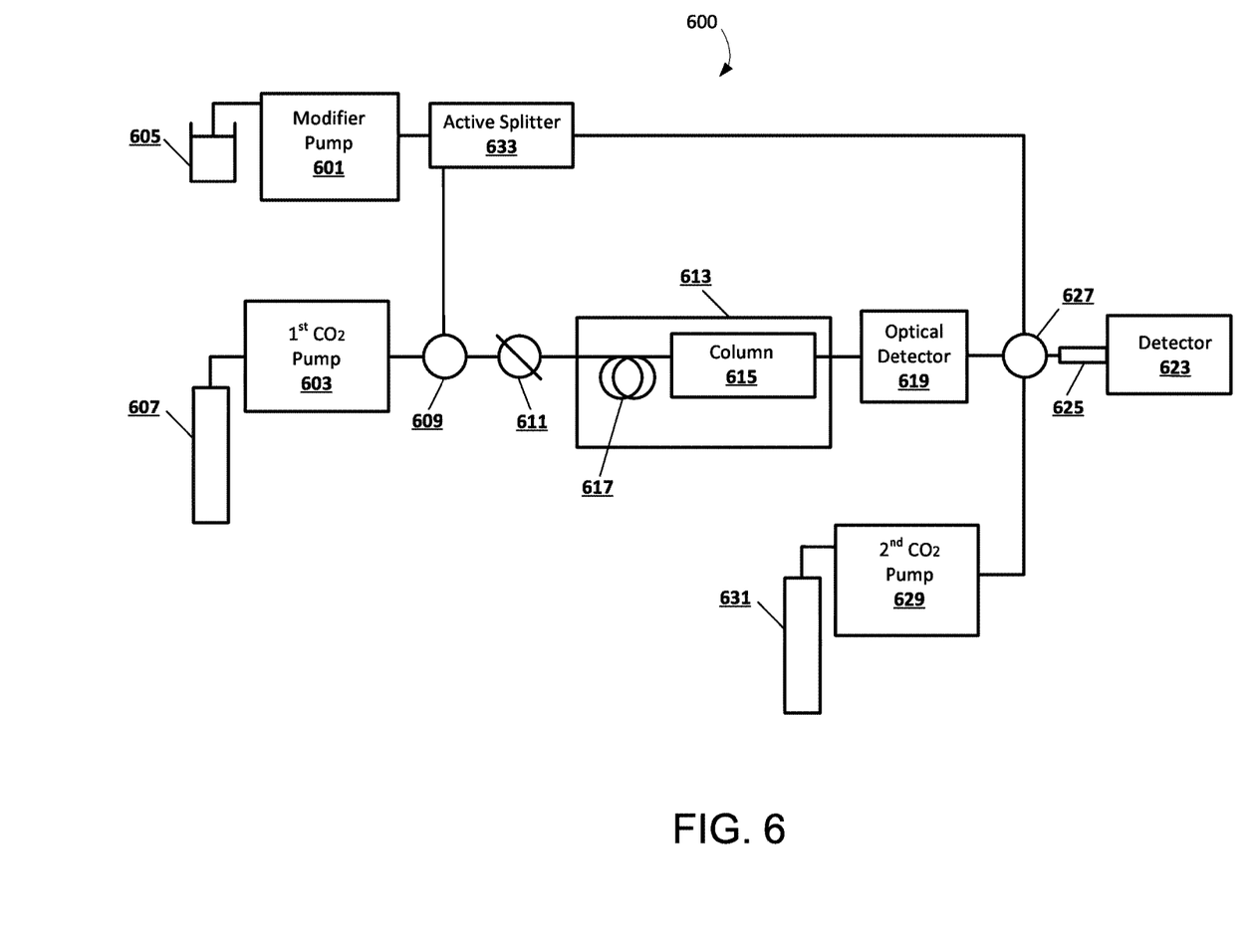
FIG. 6 is a block diagram illustrating another exemplary $CO_2$-based chromatography system with two $CO_2$ pumps, according to embodiments of the present disclosure.

FIG. 6 is a block diagram illustrating another exemplary $CO_2$-based chromatography system 600 with two $CO_2$ pumps, according to embodiments of the present disclosure. In exemplary embodiments, a second $CO_2$ pump is added to the system in place of a BPR, downstream of the chromatography column, in order to control system pressure. In this example, a modifier pump 601 is used to pump a liquid modifier from a solvent reservoir 605 to an active splitter 633, which then directs the liquid modifier to a mixer 609. A first $CO_2$ pump 603 is used to pump $CO_2$ from a $CO_2$ container 607 to the mixer 609. The liquid modifier and $CO_2$ mixture can be injected to a chromatography column 615 via a sample injector 611. The first $CO_2$ pump 603 and the modifier pump 601 are disposed to transmit a mixture of $CO_2$ and liquid modifier to the chromatography column 615 according to a gradient, and the active splitter 633 is used to control the gradient. In this example embodiment, the $CO_2$-based chromatography column 615 is located within a column oven 613, which includes preheating elements 617.

An optional optical detector 619 may be located at the output of the chromatography column 615, in some embodiments. The first $CO_2$ pump 603 is operated in constant flow mode and is responsible for maintaining a constant flow rate of the mobile phase across the column 615. A second $CO_2$ pump 629 is located downstream of the column 615 and can be connected to the system using, for example, a tee fitting 627. The active splitter 633 can also direct a liquid modifier from the modifier pump 601 to the flow stream at the output of the column 615 using the tee fitting 627. In some embodiments, the outputs of the active splitter and second $CO_2$ pump are connected to the system using a cross fitting. In exemplary embodiments, the active splitter 633 can control the liquid modifier entering the flow stream at the output of the column 615 according to a reverse gradient of the upstream gradient entering the input of the column 615 via the mixer 609 and injector 611. In some embodiments, the tubing volume connecting the active splitter to the system is designed to compensate for system volume so that the net post-column mobile phase composition remains consistent across a composition gradient. The second $CO_2$ pump 629 is operated in constant pressure mode and is responsible for maintaining the system pressure. Since the first $CO_2$ pump 603 and the second $CO_2$ pump 629 are operated independently, the system flow rate and system pressure are effectively decoupled. A fixed restrictor 625 is located downstream of the second $CO_2$ pump 629 and upstream of a detector 623. In some examples, the detector 623 is a flame ionization detector. The second $CO_2$ pump 629 can pump $CO_2$ from a second $CO_2$ container 631. As will be appreciated, the first $CO_2$ container 607 and the second $CO_2$ container 631 could be a single container, in some embodiments.

In exemplary embodiments, in order to reduce the magnitude of change of the mobile phase composition across the gradient while employing a pressure-controlled pump, a pressure controlling fluid gradient can be employed. In this particular example, the active splitter 633 can control the liquid modifier entering downstream of the column 615 according to a reverse gradient of the liquid modifier entering upstream of the column 615. In this manner, the total flow rate of liquid entering the detector 623 is constant over the entire composition-programmed gradient separation. Because a single liquid modifier fluid cannot compensate for the reduced pressure experienced when the $CO_2$ flow rate is reduced as the gradient progresses, the pressure controlling fluid is a binary mixture of $CO_2$ and liquid modifier, and the second $CO_2$ pump 629 is operated in a constant pressure mode. In this regard, the total amount of liquid entering the detector 623 is fixed, the tuning parameters are more closely matched to all regions of the gradient, and the system pressure can be accurately controlled.

Figure 7:
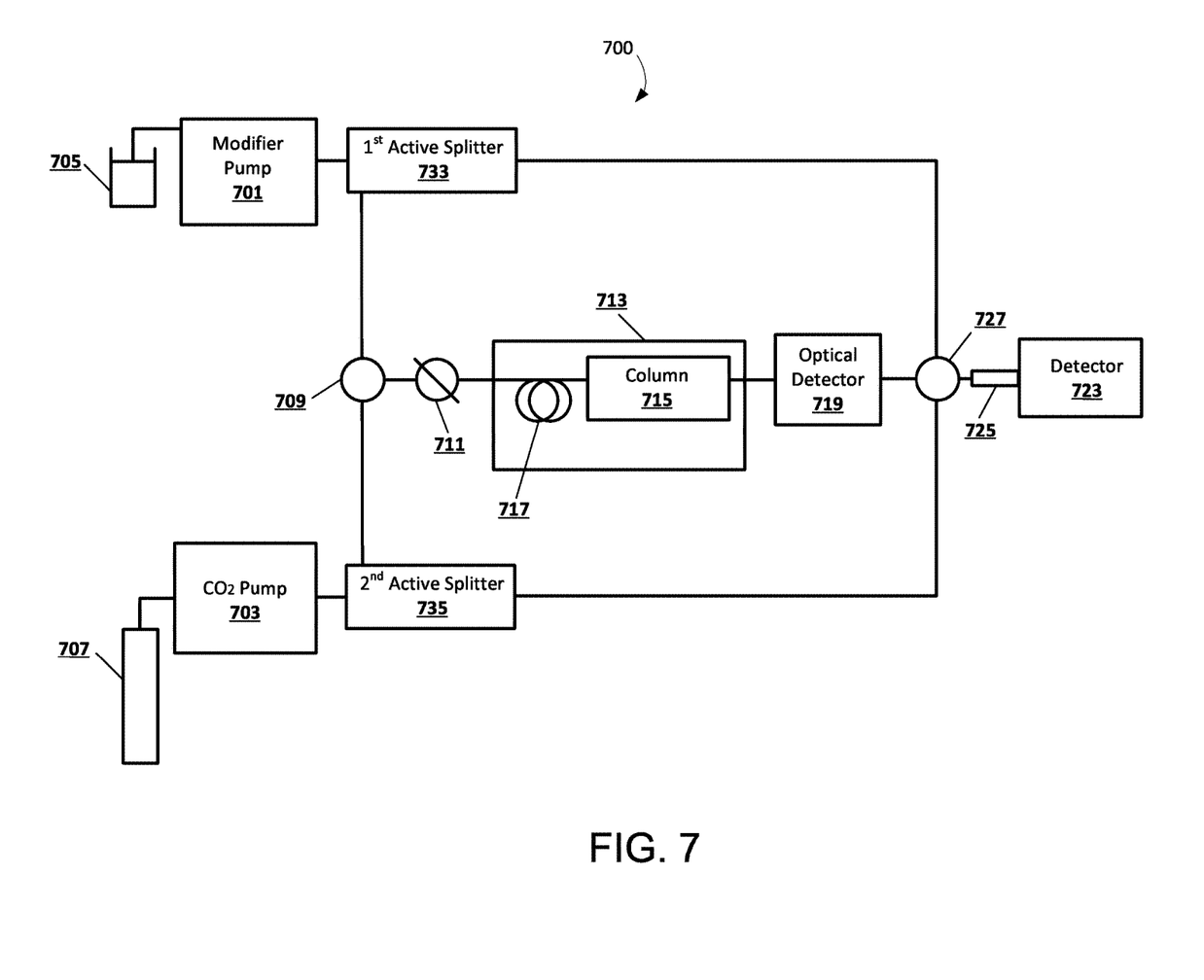
FIG. 7 is a block diagram illustrating another exemplary $CO_2$-based chromatography system with two active splitters, according to embodiments of the present disclosure.

FIG. 7 is a block diagram illustrating another exemplary $CO_2$-based chromatography system 700 with two active splitters, according to embodiments of the present disclosure. In exemplary embodiments, a modifier pump 701 is used to pump a liquid modifier from a solvent reservoir 705 to a first active splitter 733, which then directs a portion of the liquid modifier to a mixer 709. A $CO_2$ pump 703 can be used to pump $CO_2$ from a $CO_2$ container 707 to a second active splitter 735, which then directs a portion of the $CO_2$ to the mixer 709. At the mixer 709, the liquid modifier and $CO_2$ form a mixture that can be introduced to a chromatography column 715 via a sample injector 711, in some embodiments. The first active splitter 733 and the second active splitter 735 are disposed to transmit a mixture of $CO_2$ and liquid modifier to the chromatography column 715 according to a gradient. In this example embodiment, the $CO_2$-based chromatography column 715 is located within a column oven 713, which includes preheating elements 717. An optional optical detector 719 may be located at the output of the chromatography column 715, in some embodiments. The second active splitter 735 is disposed to introduce $CO_2$ to the mixer 709 and maintain a constant flow rate of the mobile phase across the column 715. The first active splitter 733 and the second active splitter 735 are also disposed to introduce liquid modifier and $CO_2$, respectively, downstream of the column 715 using, for example, a tee fitting 727. In exemplary embodiments, the first active splitter 733 can control the liquid modifier entering the flow stream at the output of the column 715 according to a reverse gradient of the upstream gradient entering the input of the column 715 via the mixer 709 and injector 711. In some embodiments, the tubing volume connecting the active splitter to the system is designed to compensate for system volume so that the net post-column mobile phase composition remains consistent across a composition gradient. The second active splitter 735 can also be responsible for maintaining the system pressure by controlling the amount of $CO_2$ introduced into the system downstream of the column 715. A fixed restrictor 725 is located downstream of the tee fitting 727 and upstream of a detector 723. In some examples, the detector 723 is a flame ionization detector.

In exemplary embodiments, in order to reduce the magnitude of change of the mobile phase composition across the gradient while employing a pressure-controlled pump, a pressure controlling fluid gradient can be employed. In this particular example, the first active splitter 733 can control the liquid modifier entering downstream of the column 715 according to a reverse gradient of the liquid modifier entering upstream of the column 715. In this manner, the total flow rate of liquid entering the detector 723 is constant over the entire composition-programmed gradient separation. Because a single liquid modifier fluid cannot compensate for the reduced pressure experienced when the $CO_2$ flow rate is reduced as the gradient progresses, the pressure controlling fluid is a binary mixture of $CO_2$ and liquid modifier, and the second active splitter 735 is operated in order to maintain a constant pressure mode to maintain a target pressure downstream of the $CO_2$-based chromatography column 715. In this regard, the total amount of liquid entering the detector 723 is fixed, the tuning parameters are more closely matched to all regions of the gradient, and the system pressure can be accurately controlled.

Figure 8A:
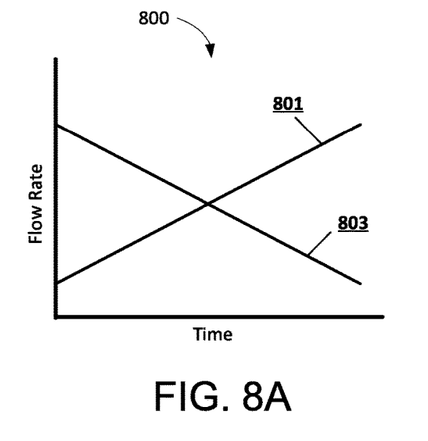
FIG. 8A is a graph of the flow rate for the upstream co-solvent and upstream $CO_2$ for a $CO_2$-based chromatography system where a binary pressure control fluid is introduced using a downstream pump, according to embodiments of the present disclosure.
Figure 8B:
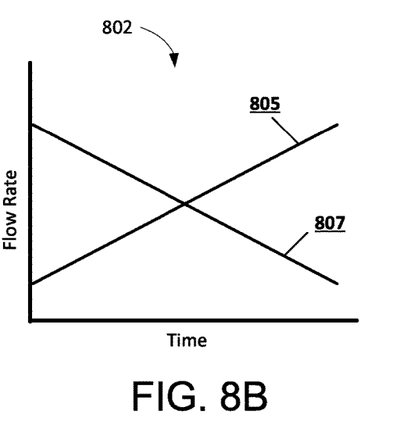
FIG. 8B is a graph of the flow rate for the downstream co-solvent and downstream $CO_2$ for a $CO_2$-based chromatography system where a binary pressure control fluid is introduced using a downstream pump, according to embodiments of the present disclosure.
Figure 8C:
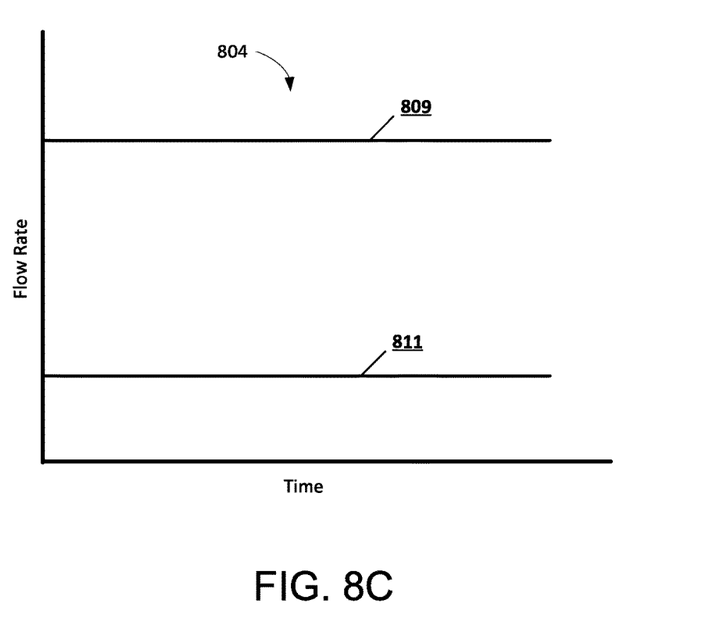
FIG. 8C is a graph of the net co-solvent flow rate and the net $CO_2$ flow rate for a $CO_2$-based chromatography system where a binary pressure control fluid is introduced using a downstream pump, according to embodiments of the present disclosure.

FIGS. 8A-8C show graphs of flow rates for a $CO_2$-based chromatography system where a binary post-column pressure control fluid is used, according to embodiments of the present disclosure. In this example embodiment, the binary pressure control fluid includes a co-solvent and $CO_2$, where the co-solvent is added as an inverse gradient of the upstream co-solvent. FIG. 8A shows a graph 800 of the flow rate for the upstream co-solvent and upstream $CO_2$ for a $CO_2$-based chromatography system where a binary pressure control fluid is introduced using a downstream pump, according to embodiments of the present disclosure. FIG. 8B is a graph 802 of the flow rate for the downstream co-solvent and downstream $CO_2$ for a $CO_2$-based chromatography system where a binary pressure control fluid is introduced using a downstream pump, according to embodiments of the present disclosure. FIG. 8C is a graph of the net co-solvent flow rate and the net $CO_2$ flow rate for a $CO_2$-based chromatography system where a binary pressure control fluid is introduced using a downstream pump, according to embodiments of the present disclosure. As the gradient progresses, graph 801 shows an increase in upstream co-solvent flow rate and graph 803 shows a decrease in upstream $CO_2$ flow rate. Graph 807 shows how the downstream co-solvent is introduced to the system according to a reverse gradient compared to the upstream co-solvent shown in graph 801. The downstream $CO_2$ flow rate is shown in graph 805. As discussed above, the downstream co-solvent, or liquid modifier, is introduced using a downstream pump operating in constant pressure mode. The net $CO_2$ flow rate, shown in graph 811, and the net co-solvent flow rate, shown in graph 809, show how the net co-solvent flow rate and net $CO_2$ flow rate remain substantially constant throughout the entire gradient process. This consistency in co-solvent flow rate can provide increased accuracy and uniformity of response at the detector.

Figure 9:
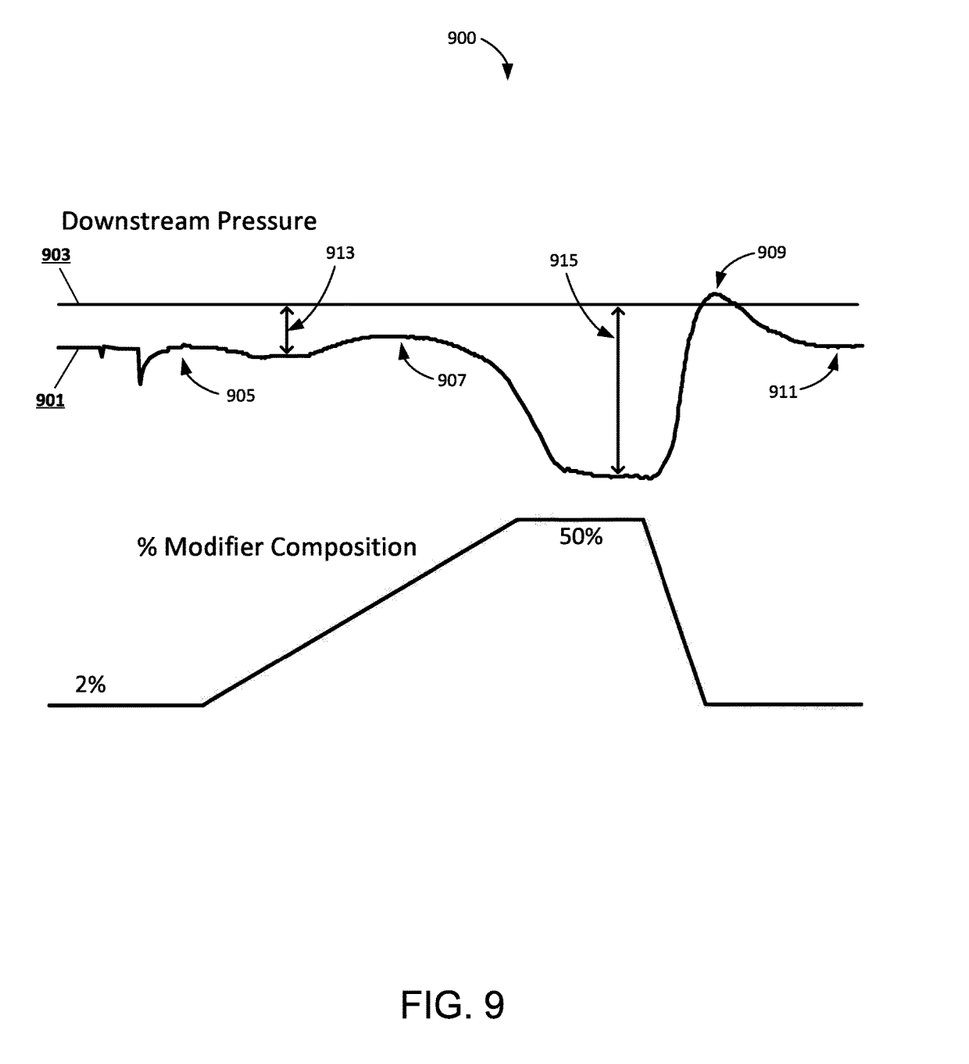
FIG. 9 is a graph representing the relationship between mobile phase composition and back pressure generated by a fixed restrictor.

FIG. 9 is a graph 900 representing the relationship between mobile phase composition and back pressure generated by a fixed restrictor. FIG. 9 illustrates the ability of the systems disclosed herein to normalize system pressure during a composition-programmed gradient separation. As can be seen in this embodiment, the graph 901 illustrates the downstream pressure generated by the fixed restrictor. In this example, the downstream pressure begins at about 1,810 PSI at region 905 when the modifier composition is around 2% and slowly increases to about 1,860 PSI in region 907 as the composition of the mobile phase approaches 30%. In order to maintain the downstream pressure at about 2,000 PSI, indicated at 903, only a small amount of pressure control fluid needs to be added in order to make up the difference in pressure at 913. When the modifier composition reaches about 50%, the downstream pressure drops to about 1,230 PSI, and a large addition of pressure control fluid is required in order to make up the difference in pressure shown at 915. After the modifier percentage drops again, the downstream pressure spikes to about 2,030 PSI in region 909. Once the modifier percentage has dropped to about 2%, the downstream pressure returns to about 1,810 PSI at region 911.

In exemplary embodiments, a fixed restrictor can be used to connect the tee fitting to the detector, described above in reference to FIGS. 5 and 6. The fixed restrictor can ensure appreciable density of the mobile phase until the analyte has reached the detector. Because this design is of very low dead volume, a split-flow interface is not necessary when interfacing to a low-pressure detector. In a mass spectrometer, the ion source must be 'tuned' to optimize ionization efficiency in order to maximize sensitivity. Tuning involves optimizing factors such as capillary voltage, desolvation gas flow rate, desolvation gas temperature, and the probe position relative to the mass spectrometer inlet. These tuning factors are all dependent on the flow rate and composition of the mobile phase entering the ion source. As such, changes in the mobile phase require re-optimization of the tuning factors in the ion source. For isocratic elution, the mobile phase composition does not change during the chromatographic run and the mass spectrometer can be tuned for optimal response over all regions of the separation. Conversely, under a gradient elution profile, the mass spectrometer must be tuned at one spot in the gradient. In this case, while the mass spectrometer is optimized for the one point in the gradient, it will not be tuned for other parts of the gradient. This is especially problematic in $CO_2$-based chromatography systems, since the amount of liquid co-solvent entering the source can change an order of magnitude or more over the course of a gradient-programmed separation. Employing the pressure-controlling fluid interface can exaggerate this issue. As shown in FIG. 9, there is a larger amount of post-column fluid added near the end of the gradient where the amount of co-solvent is highest at around 50%. Therefore, the change in mobile phase composition changes more dramatically with the pressure-controlling fluid interface as compared to a separation with a BPR (i.e. a split-flow interface). As such, the ideal mass spectrometer tuning parameters between different regions of the gradient can be large, thereby reducing sensitivity for some analytes. By using a binary pressure control fluid, as described herein, where the co-solvent is introduced according to a reverse gradient of the upstream co-solvent and the $CO_2$ is introduced in a constant pressure mode, the flow rate can be maintained constant and detector sensitivity maintained.

Figure 10:
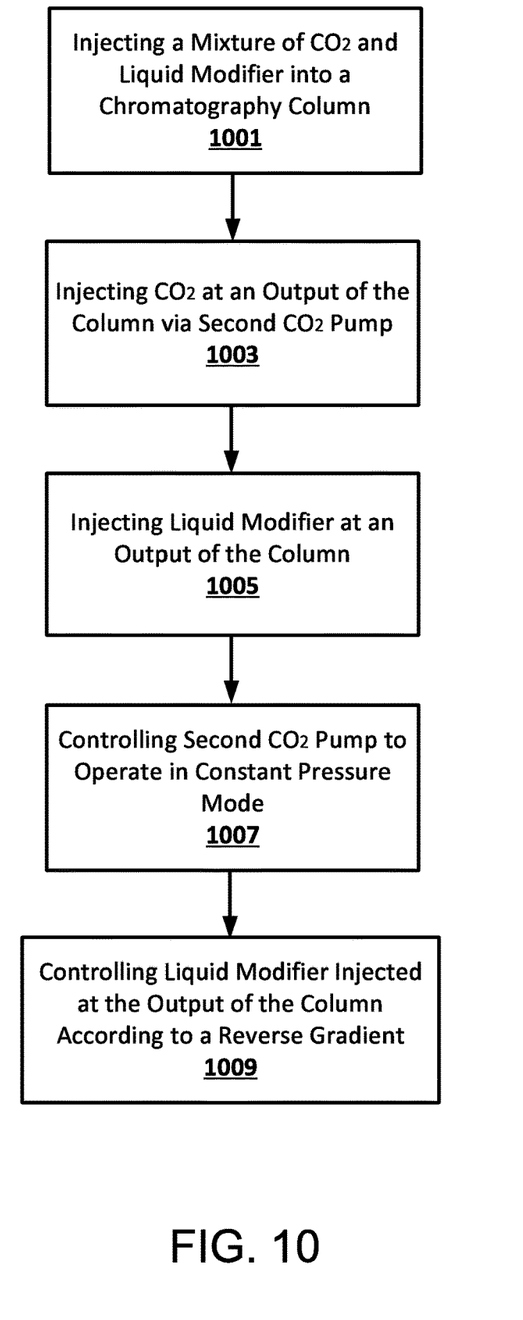
FIG. 10 is a flow chart of an exemplary method of maintaining pressure in a $CO_2$-based chromatography system, according to an embodiment of the present disclosure.

FIG. 10 is a flow chart of an exemplary method for maintaining pressure in a $CO_2$-based chromatography system, according to an embodiment of the present disclosure. In step 1001, a mixture of $CO_2$ and liquid modifier is introduced into a $CO_2$-based chromatography column. As discussed above, the liquid modifier can be introduced into the system according to a composition-programmed gradient. The $CO_2$ is introduced into the system using a first $CO_2$ pump that operates in a constant flow mode. In exemplary embodiments, the mixture of $CO_2$ and liquid modifier is introduced into the $CO_2$-based chromatography column via a mixer.

In step 1003, $CO_2$ is introduced into the flow stream at the output of the $CO_2$-based chromatography column using a second $CO_2$ pump. The second $CO_2$ pump operates independently of the first $CO_2$ pump.

In step 1005, liquid modifier is introduced into the flow stream at the output of the $CO_2$-based chromatography column. In exemplary embodiments, die liquid modifier is introduced into the column using a first liquid modifier pump, and a second liquid modifier pump is used to introduce the liquid modifier at the output of the $CO_2$-based chromatography column. In other embodiments, an active splitter can be disposed to receive liquid modifier from a single liquid modifier pump, and the active splitter delivers liquid modifier to the chromatography column and also delivers liquid modifier at the output of the column.

In step 1007, the second $CO_2$ pump is controlled to operate in constant pressure mode to maintain a target pressure downstream of the $CO_2$-based chromatography column. In exemplary embodiment, the second $CO_2$ pump maintains system pressure downstream of the column at a target value.

In step 1009, the amount of liquid modifier introduced at the output of the column is controlled according to a reverse gradient compared to the gradient introduced into the column. In exemplary embodiments, the liquid modifier introduced at the output of the column and the $CO_2$ introduced from the second $CO_2$ pump are introduced at the output of the column via a tee fitting. The output of the tee fitting can be directed to a detector via a fixed restrictor, in some embodiments. In embodiments where a first liquid modifier pump is used to introduce liquid modifier into the column and a second liquid modifier pump is used to introduce liquid modifier at the output of the column, the second liquid modifier pump is configured to introduce liquid modifier at the output of the column according to a reverse gradient compared to the gradient introduced into the column. In embodiments where a single liquid modifier pump is used in connection with an active splitter, the active splitter is configured to control the gradient introduced into the column and also control the amount of liquid modifier introduced at the output of the column according to a reverse gradient compared to the gradient introduced into the column. In some embodiments, the output of the column, the $CO_2$ introduced from the second $CO_2$ pump, and the liquid modifier introduced at the output of the column are directed to a detector. The detector can be, for example, a flame ionization detector or a mass spectrometer. In exemplary embodiments, the amount of liquid modifier introduced at the output of the column is controlled such that the total flow rate of liquid modifier entering the detector is constant.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

In alternative embodiments, the techniques described above with respect to pumps used in $CO_2$-based chromatography systems may be applicable to pumps used in other types of chromatography systems that include mobile phases that vary greatly in density with minor changes in temperature. For example, a mobile phase including methanol at extremely high pressures, such as pressures within an area on a pressure-temperature plot defined approximately by the points (500 PSI, 200° C.), (15,000 PSI, 400° C.), (1,000 PSI, 400° C.), may in some instances benefit from added temperature or pressure control. In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

What is claimed is:

1. A method of maintaining pressure in a $CO_2$-based chromatography system, the method comprising:
   introducing $CO_2$ into a mixer via a first $CO_2$ pump;
   introducing liquid modifier into a mixer via a first liquid modifier pump;
   receiving a mixture of CO2 and liquid modifier from the mixer at a chromatography column;
   introducing $CO_2$ into a flow stream at an output of the column via a second $CO_2$ pump;
   introducing liquid modifier into the flow stream at the output of the column via a second liquid modifier into pump;
   controlling the second $CO_2$ pump to deliver liquid modifier according to a reverse pressure downstream of the column; and
   controlling the second liquid modified pump to deliver liquid modifier according to a reverse gradient compared to a gradient introduced into the column from the first liquid modifier pump.

2. The method of claim 1, further comprising introducing the flow stream at the output of the column into a detector.

3. The method of claim 2, further comprising controlling the second liquid modifier pump such that a total flow rate of liquid modifier entering the detector is constant.

4. The method of claim 2, wherein the detector is a flame ionization detector or a mass spectrometer.

5. The method of claim 1, wherein the first $CO_2$ pump operates in a constant flow mode, and the second $CO_2$ pump operates in a constant pressure mode.

6. The method of claim 1, wherein the second $CO_2$ pump and the second liquid modified pump introduce fluid into the flow stream at the output of the column via a tee fitting.

7. The method of claim 1, wherein the second $CO_2$ pump and the second liquid modifier pump introduce fluid into the flow stream at the output of the column via a tee fitting.

8. The method of claim 7, further comprising directing an output of the tee fitting to a detector via a fixed restrictor.

9. A $CO_2$-based chromatography system comprising:
   a first $CO_2$ pump disposed to deliver $CO_2$ to a chromatography column;
   a liquid modifier pump;
   a second $CO_2$ pump located downstream of the column and disposed to operate independently of the first $CO_2$ pump to introduce $CO_2$ into a flow stream at an output of the column, the second $CO_2$ pump operating in constant pressure mode in order to maintain a target pressure; and
   an active splitter disposed to receive a liquid modifier from the liquid modifier pump, the active splitter disposed to deliver liquid modifier to the chromatography column according to a gradient, and further disposed to introduce liquid modifier into the flow stream at the output of the column according to a reverse gradient compared to the gradient entering the chromatography column.

10. A $CO_2$ based-pump system comprising:
    a $CO_2$ pump;
    a liquid modifier pump;
    a first active splitter disposed to receive a liquid modifier from the liquid modifier pump, introduce the liquid modifier to a chromatography column according to a gradient, and introduce the liquid modifier into a flow stream downstream of the chromatography column according to a reverse gradient compared to the gradient entering the chromatography column; and
    a second active splitter disposed to receive $CO_2$ from the $CO_2$ pump, introduce $CO_2$ to the chromatography column, and introduce $CO_2$ into the flow stream downstream of the chromatography column to maintain a target pressure.

* * * * *